US008614789B2

(12) United States Patent
Noblett et al.

(10) Patent No.: US 8,614,789 B2
(45) Date of Patent: Dec. 24, 2013

(54) MICROPLATE MOUNT SYSTEM AND SENSING METHODS

(75) Inventors: David Noblett, Naperville, IL (US); Robert E. Krug, Naperville, IL (US); Steven Liebold, Palatine, IL (US); Mark Francis Krol, Painted Post, NY (US); David Andrew Pastel, Horseheads, NY (US); Ravi Marala, Painted Post, NY (US); Ken Neumann, Naperville, IL (US); Dawn Neumann, legal representative, Naperville, IL (US)

(73) Assignees: PerkinElmer Health Sciences, Inc, Waltham, MA (US); Corning Incorporated, Corning, NY (US)

( * ) Notice: Subject to any disclaimer, the term of this patent is extended or adjusted under 35 U.S.C. 154(b) by 173 days.

(21) Appl. No.: 13/032,303

(22) Filed: Feb. 22, 2011

(65) Prior Publication Data

US 2011/0273706 A1   Nov. 10, 2011

Related U.S. Application Data

(60) Provisional application No. 61/306,640, filed on Feb. 22, 2010.

(51) Int. Cl.
*G01N 21/01* (2006.01)
(52) U.S. Cl.
USPC ............ 356/244; 356/614; 356/246; 356/440
(58) Field of Classification Search
USPC ................. 356/244, 246, 432–440, 614–623; 435/7.92, 287.3
See application file for complete search history.

(56) References Cited

U.S. PATENT DOCUMENTS

| | | | |
|---|---|---|---|
| 5,345,395 A | 9/1994 | Griner | |
| 2004/0168919 A1 | 9/2004 | Kurt et al. | |
| 2005/0052646 A1* | 3/2005 | Wohlstadter et al. | 356/311 |
| 2005/0231714 A1* | 10/2005 | Hudson | 356/246 |
| 2007/0020152 A1 | 1/2007 | Costello, III et al. | |
| 2007/0077181 A1* | 4/2007 | Youngbear | 422/102 |
| 2008/0199365 A1 | 8/2008 | Chu | |
| 2009/0155823 A1 | 6/2009 | Bunce et al. | |

FOREIGN PATENT DOCUMENTS

EP        1190233        3/2002

* cited by examiner

*Primary Examiner* — Hoa Pham
(74) *Attorney, Agent, or Firm* — Cesari and McKenna, LLP

(57) ABSTRACT

The invention is a microplate mounting system for mounting a microplate relative to an optical reader to control an angle of incidence of an interrogation beam at the microplate and includes a reference plane with at least one set of mount features that engage one or both of the bottom of the microplate and the skirt of the and a first positioning mechanism that provides a reversible and predetermined separation in the z direction between a plane formed by the bottom of the microplate and the reader, to control the angle of incidence of the interrogation beam at the microplate by reversibly controlling the relative positioning of the microplate in the z direction through the engagement between the bottom and/or skirt of the microplate and the at least one set of mount features.

25 Claims, 8 Drawing Sheets

MICROPLATE MOUNT SYSTEM AND SENSING METHODS

CROSS-REFERENCE TO RELATED APPLICATIONS

The present application claims the benefit of U.S. Provisional Patent Application Ser. No. 61/306,640, which was filed on Feb. 22, 2010, by Mark Francis Krol for a MICROPLATE MOUNT SYSTEM AND SENSOR METHOD and is hereby incorporated by reference.

BACKGROUND OF THE INVENTION

1. Field of the Invention

The disclosure relates generally to a microplate mount system and methods of making and using the system.

2. Background Information

At the present time, existing technology utilizes various instrumentation to measure photometric properties such as color, absorbance, intensity, and photoluminescence at specific locations on a microplate surface where chemical and biological samples are associated. For example, optical readers are commonly used in biological fields such as genetic research, drug discovery, or diagnostic purpose to detect hundreds or thousands of compounds (e.g., DNA, oligonucleotides, proteins, etc.) typically deposited on a surface of a substrate (e.g. a glass slide) in an array configuration. It is well known in the art that proper alignment of the microplate holding the samples and the light beam of the optical device is necessary to perform many photometric measurements.

Similarly, to perform image analysis, devices such as optical scanners/readers and microscopes demand sample stages that provide consistent and accurate positioning of the microplate. Moreover, for imaging devices that utilize sensors, waveguide gratings or other microdevices on a sample surface of a substrate, alignment of the surface having correlation with an optical component is critical for consistent measurements.

Many photometric instruments make use of a multi-site microplate to prepare a large number of test samples. Microplates are typically rectangular structures made of glass or plastic, each having a plurality of wells for holding sample material. The plate itself is generally inexpensive, safe, sturdy, and convenient to handle. They are disposable, but can be cleaned easily and may be reused when necessary.

As chemical and biological sample size decreases and the number of samples increases on an array surface, alignment of the samples relative to the measuring instrument becomes progressively more important. Present and future drug discovery relies on a large number of test sites within an array. For example, to identify a specific protein sequence for a binding event with a certain type of receptor, a high density of samples is needed to expose the receptor to an many different permutations of proteins as possible. Therefore, the samples to be assayed are located on the surface in a multitude of discrete locations, each location containing a single sample. A standard microplate is typically about 127.76 mm in length×85.48 mm in width and may accommodate up to 96, 384 or even 1536 assays. Because of the small size and close spacing of the analyte samples, the microplate sample surface must be precisely and repeatedly aligned with respect to the measuring apparatus, thus allowing the measuring apparatus to make error-free measurements of the samples.

Systems are currently being developed to detect the binding of molecular species without adding labels. These systems utilize disposable microplates having sensors embedded at specific locations and a reader to interrogate those precise localities of the microplate. The utility of assays performed in such systems relies on making successive analytical observations interplayed between steps in the assay. This way, a true "before and after" analysis may be accomplished revealing the occurrence (or absence) of biological or chemical molecular interactions. Therefore, the repeatable and consistent alignment and/or positioning of a microplate incorporated into or onto a stage for analytical interrogation is crucial and necessitated by these newly developed systems.

Current measurement protocol requires four primary steps: (1) initial/background measurement, (2) removal of the plate (for additional assay steps), (3) reinsertion of the plate into the reader, (r) second measurement, and (5) comparison of first and second measurements. Following the placement of a microplate into an exact location, an initial measurement can be read by a photometric/optical instrument. Once the microplate is removed, and manipulation of its contents completed, examination of the microplate depends on the exact repositioning of the microplate into the reader. Therefore, the second/final measurement result can be adversely affected by the slightest change, rotational and/or translational, in microplate position between the initial and second/final measurement steps.

Corning, Inc., has developed and marketed the Epic® system, a label-free microplate based drug discovery tool. The Epic® technology is based on resonant waveguide grating (RWG) sensor technology. The RWG sensors are sensitive to the incidence angle of the interrogating optical signal, and as a result, the incidence angle of the interrogating optical signal on the RWG sensor must be adequately controlled to achieve acceptable performance of the sensor and reader system. In certain commercial Epic® systems the incidence angle can be controlled by, for example, using high precision stages and a precision plate nest, see for example, U.S. Patent Application Publication No. 2007/0020152, which is incorporated herein in its entirety by reference. While these components can provide adequate control of the interrogating optical signal incidence angle, the required stages can be costly, occupy a large physical volume, rely upon peripheral or auxiliary services, and rely upon extremely flat and stable mounting surfaces. These aspects of controlling the interrogating optical signal incidence angle can result in increased system cost and complexity.

SUMMARY OF THE INVENTION

The invention is a microplate mounting system for mounting a microplate relative to an optical reader to control an angle of incidence of an interrogation beam at the microplate and includes a reference plane with at least one set of mount features that engage the bottom and/or skirt of a microplate and a first positioning mechanism that provides a reversible and predetermined separation in the z direction between a plane formed by the bottom of the microplate and the reader to control the angle of incidence of the interrogation beam at the microplate by reversibly controlling the relative positioning of the microplate in the z direction through the engagement between the bottom and/or skirt of the microplate and the at least one set of mount features.

The microplate may be lowered into engagement with the mount features or the mount features may be raised into engagement with the bottom and/or skirt of the microplate, and the reference plane may be elevated or lowered before or after the engagement to position the microplate at a desired z displacement from the reader.

A microplate carrier may operate in cooperation with the first positioning mechanism and release the microplate to the control of the mounting features at least while the microplate is being displaced through its engagement with the mounting features. The carrier may re-grip the microplate, as necessary to maintain lateral alignment, during interrogation operations.

A second positioning system may be utilized to move the microplate laterally with respect to the reference plane to positions for interrogation. The second positioning system thus moves the microplate to desired x and y positions relative to the interrogating beam in systems in which the reader can interrogate only a portion of the microplate at a given time. The second positioning system similarly operates in cooperation with the first positioning system to move the microplate when the microplate is not engaging the mount features. Once the second positioning mechanism has moved the plate to a next interrogation position, the first positioning mechanism operates to control the z displacement of the plate relative to the reader in order to control the angle of incidence.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
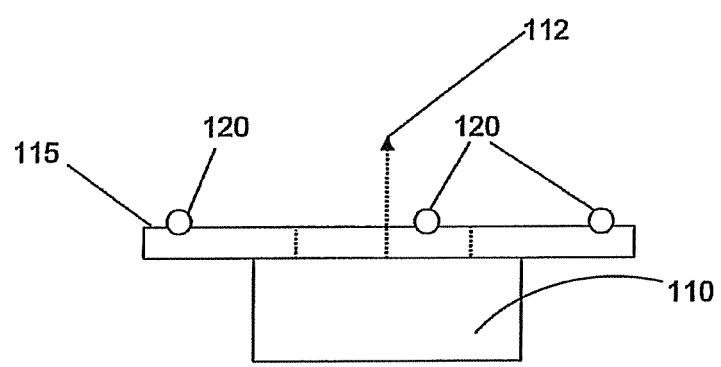
FIG. 1 provides a schematic showing a mechanical reference plane with mounting features and having a reader aperture therethrough in combination with an optical reader.

Various embodiments of the disclosure will be described in detail with reference to drawings. Reference to various embodiments does not limit the scope of the invention, which is limited only by the scope of the claims attached hereto. Additionally, any examples set forth in this specification are not limiting and merely set forth some of the many possible embodiments for the claimed invention.

DEFINITIONS

"Microplate," "plate," "microarray," or like terms refer, for example, to a transparent base and a holey plate attached to the base to form one or more wells. A sensor element can optionally be situated in the bottom of one or more of the wells and contact media can be placed in the well to detect selected analyte or like interactions in the space near the surface of the sensor. The disclosed apparatus and its disclosed various configurations can be used for processing or handling, for example, any standard plate or custom plate. The plate need not include a sensor element.

"Include," "includes," or like terms means encompassing but not limited to, that is, inclusive and not exclusive.

"Consisting essentially of" in embodiments refers, for example, to a disclosed mounting system or method thereof, and articles, devices, or any apparatus of the disclosure, and can include the components or steps listed in the claim, plus other components or steps that do not materially affect the basic and novel properties of the articles, apparatus, or methods of making and use of the disclosure, such as particular components, particular mechanisms, a particular agents, a particular use condition, or like structure, material, or process variable selected. Items that may materially affect the basic properties of the components or steps of the disclosure, or that may impart undesirable characteristics to aspects of the disclosure include, for example, expensive, bulky, or complex mechanical componentry that does not provide adequate incident beam angle control nor precision relative vertical and horizontal movement of a microplate relative to an optical reader.

The indefinite article "a" or "an" and its corresponding definite article "the" as used herein means at least one, or one or more, unless specified otherwise.

Abbreviations, which are well known to one of ordinary skill in the art, may be used (e.g., "h" or "hr" for hour or hours, "uRad" for microRadians, "mRad" for milliRadians, "mL" for milliliters, "nm" for nanometers, and like abbreviations).

Specific and preferred values disclosed for components, subsystems, systems, assemblies, times, speeds, and like aspects, and ranges thereof, are for illustration only; they do not exclude other defined values or other values within defined ranges. The apparatus and methods of the disclosure include those having any value or any combination of the values, specific values, more specific values, and preferred values described herein.

In embodiments of the disclosure, the issue of cost and complexity of providing adequate control of the interrogating optical signal incidence angle for an optical or like reader system can be overcome by, for example, a plate mount system having kinematic or other mounting features and low-precision or precision relative motion between the plate and the reader.

In embodiments, the disclosure provides a mount system for a label-free microplate-based sensing system. The system can use kinematic mounting principles and low-precision relative motion between a microplate and a corresponding reader to control the interrogating optical beam incidence angle at the label-free sensors located at the bottom of the wells of the microplate. With the angle controlled, the lateral movement of the plate may be made by relatively low precision shuttles.

In embodiments, the disclosure provides: 1) a means to control the interrogating optical signal incidence angle at the sensors without the need for expensive precision mechanical stage and plate nest combinations; and 2) a system having lower cost, lower complexity, and greater operational robustness, compared to available systems. The present system can be used, for example, in low-throughput resonance waveguide grating applications, or like applications.

In embodiments, the disclosure provides a mount apparatus subsystem for use, for example, in a label-free microplate based sensing system. The mount system uses kinematic or other mount features and low-precision relative motion between the label-free microplate and the corresponding optical reader to control the interrogating optical signal incidence angle at the label-free sensors embedded-in or situated-on the bottom of wells of the microplate. A particularly useful aspect of the disclosure is that the system and methods can provide control of the interrogating optical signal incidence angle without the need for precision mechanical stages. In embodiments, the interrogating optical signal incidence angle at the sensors can be positioned or maintained at a normal incidence, i.e., 90° or orthogonal to the plane of the microplate. In embodiments, the interrogating optical signal incidence angle at the sensors can be positioned or maintained at, for example, from about 80 to about 90 degrees, from about 85 to about 90 degrees, and from about 89 to about 90 degrees, relative to the plane of the microplate, including intermediate values and ranges.

In embodiments, the disclosure provides a microplate mount system comprising:

a microplate with a bottom;

a reference plane having at least one set of mount features; and a positioning mechanism that provides a reversible and predetermined separation in the z direction between a plane formed by the bottom of the microplate at the microplate and the reader to control the angle of incidence of the interrogation beam at the microplate by reversibly controlling the relative positioning of the microplate in the z direction through an engagement between the bottom and/or a skirt of the microplate and one of the at least one sets of mount features.

The relative separation motion can be, for example, a vertical displacement of the plane of the microplate towards or away from the reader.

The set of mount features comprise from 3 to about 10 features, and from 5 to about 8 features, and from 6 to about 7 features, such as spheres, pins, vias, and like elements, or a combination thereof, attached to the reference plane. The mount features can, for example, protrude from the reference plane, can be partially embedded in the reference plane, or a combination thereof.

The first positioning mechanism can be, for example, at least one of a cam, a cantilever, a spring, a manual or automated elevator, a linear actuator having a screw drive or belt drive and/or an encoder, a stepper motor, and like mechanisms, or a combination thereof. In embodiments, hard stops can be set up for the desired microplate location, and the stepper motor can be used to move the plate until it encounters one of the stops.

The mechanism for relative separation motion (z-displacement movement) can be, for example, integral to the reference plane, integral to the plate carrier, integral to the microplate reader, or a combination thereof. In this context "integral" refers to, for example, attached-to or connected-to, and like relationships. The system can further comprise, for example, an optional second positioning mechanism that provides relative lateral alignment motion (x-y plane movement) between the microplate and the reference plane, that is, sliding or translational motion for plate scanning.

In embodiments, an example method and apparatus of the second positioning mechanism that provides relative lateral alignment motion between the microplate and the reference plane can be, for example, a simple slide with a hard stop, and a screw drive or belt drive with stepper motor and encoder. A significant aspect of the second positioning mechanism is that the lateral movement does not need to be precise. The x-y motion does not need to be precise because when a micro-electro-mechanical system scanning method is utilized for beam scanning the microplate the system is relatively translationally insensitive, for example, a location error of about 200 micrometers is acceptable, when the angle of incidence is adequately controlled.

Figure 9:
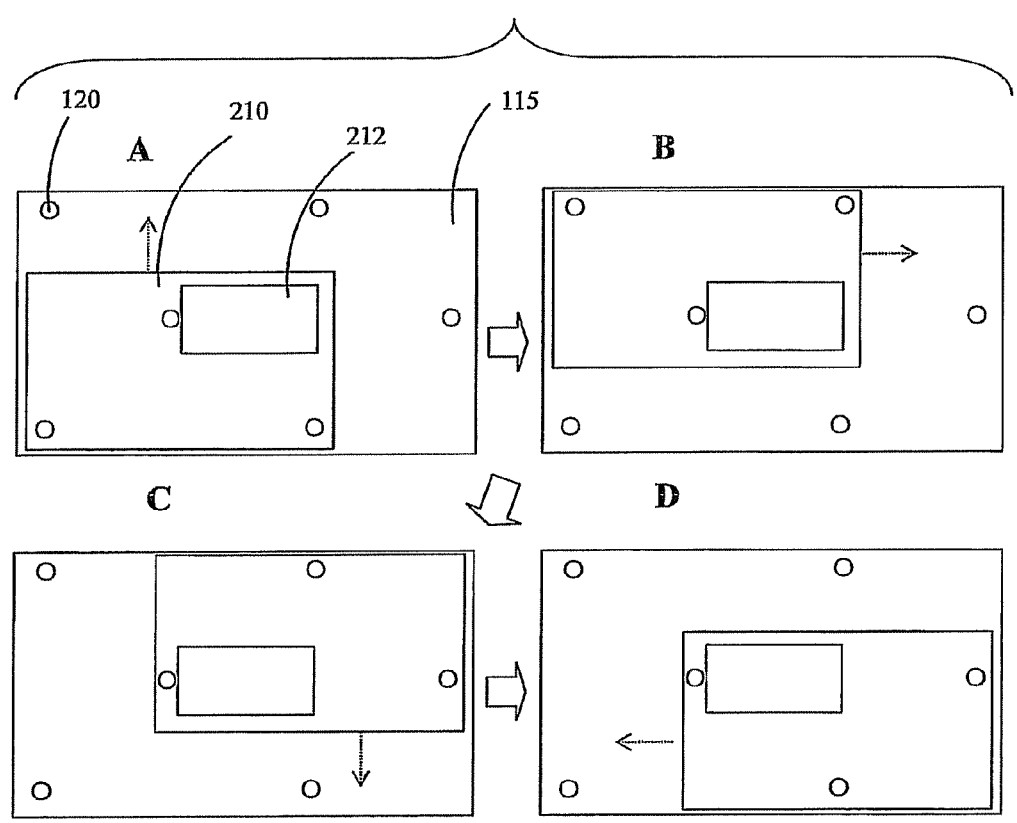
FIGS. 9A to 9D schematically show a microplate in four different read positions on the quarter-plate optical reader of FIG. 8.

The relative lateral alignment motion of the planes of the microplate and the reference plane can be, for example, vibrational, such as a simple harmonic, a complex harmonic, or translational, such as circular, elliptical, rectangular, and like movements, or a combination thereof. A particularly useful movement is a lateral motion, that is, for example, simple rectilinear motion about the interrogating beam aperture as illustrated in a sequence depicted in FIG. 9.

In embodiments, the second positioning mechanism can move the microplate about at least a portion of an aperture in the reference plane that permits the optical reader to illuminate the base of the microplate with an incident beam and to receive light from the base of the microplate from the reflected beam. The first positioning mechanism maintains the desired angle of incidence at the microplate when the microplate is in the various positions for interrogation.

The set of mount features can be, for example, an insert member having at least three mount features on each side of the insert, the insert being situated between the reference plane and the microplate. In embodiments, the insert member can have, for example, six (6) mount features on one side or both sides of the insert.

In embodiments, the system can further include, for example, at least one of: the reference plane having a recess adapted to receive at least one of the mount features on the insert, the microplate having a recess adapted to receive at least one of the mount features on the insert, or a combination thereof. The system can further include, for example, a second positioning mechanism providing relative lateral alignment motion between the microplate and the reference plane. The second positioning mechanism can move the microplate about at least a portion of an aperture in the reference plane.

In embodiments, the disclosure provides a method of using the above described microplate mounting system comprising, for example:

providing relative lateral alignment motion between the microplate and the reference plane when the microplate bottom and/or skirt and the mounting features are not engaged, and when lateral movement is completed, engaging the microplate bottom and/or skirt and the mounting features to control the angle of incidence.

The positioning can be accomplished by, for example, reducing or increasing the relative separation between the reference plane and the microplate. In embodiments, the method can further comprise, for example, providing relative lateral alignment motion between the microplate and the reference plane, i.e., sliding or translational motion for scanning. The relative alignment motion can move the microplate in a plane parallel to the reference plane, and alternatively or additionally, in a concentric or in a rectangular eccentric pattern about the aperture in the reference plane. Additionally or alternatively, the relative lateral alignment motion can move the microplate about at least a portion of an aperture in the reference plane. The first and second positioning mechanisms work in cooperation to provide the lateral movement to and thereafter the controlled angle of incidence at the various microplate positions required for interrogation.

In embodiments, the method can further include, for example, removing the microplate from the carrier that positions the microplate relative to the reference plane, and reinserting the same microplate or a different microplate (of the same make or model) into the carrier, with the relative z-displacement of the plane represented by the bottom of the reinserted microplate varying from the original level of the microplate plane by from about 1 to about 500 microRadians, from about 10 to about 500 microRadians, and from about 30 microRadians to about 300 microRadians.

In embodiments, the disclosed apparatus includes at least three cooperating components: a microplate; a mechanical reference plane with a set of mount features; and a mechanism that controls the relative z direction separation between the bottom of the microplate and an optical reader through engagement of the bottom of the microplate and the mount features. As appropriate, the reference plane is moved after the engagement, to further elevate or lower the microplate relative to the reader.

The reference plane can be adapted to receive, for example, an optical reader device or like device. The reference plane can be further adapted to permit an optical beam from the optical reader device to project through an aperture in the reference plane. The optical beam can be used to interrogate one or more sensors situated at the bottoms of wells in a microplate when the microplate is engaged with the reference plane.

The mechanical reference plane can be integral-to or integrated-with an interrogating optical reader. Referring to the Figures, FIG. 1 shows a schematic of one exemplary mount system having an optical reader 110, an interrogating beam 112, an integral mechanical reference plane 115, and mount features 120. The integral mechanical reference plane 115 can take a variety of forms. In embodiments, the reference plane can be, for example, a separate plate that is mounted directly to the optical reader or it can be a mounting plate that is part of a larger assembly or instrument. Independent of the particular implementation, the plane 115 provides a mechanical reference relative to the optical reader, or more particularly, a mechanical reference plane relative to the interrogating optical beam 112 from the reader. As shown, the reference plane 115 includes a reader aperture 212 through which the optical beam 112 is directed.

In embodiments, the system includes a set of mounting features 120 (e.g., ball bearings, pins, vias, and like features) that are located on the mechanical reference plane. FIG. 1 also shows the mount features as spheres, such as rigid metal balls, on which the microplate can rest. For an Epic® label-free microplate, the kinematic ball mounts contact the bottom of the microplate insert or a skirt attached to the microplate. Three mounting features can be used to accurately and repeatedly set a plane represented by the bottom of the microplate. More than three kinematic features can be used, if desired, but the system may become mechanically or dimensionally overconstrained. The kinematic mount features can take a variety of forms other than the balls shown in FIG. 1, for example, a cone, a cone with balls, a post with a ball or balls, a post with a spherical or rounded end, a pin, and like structures.

Figure 2:
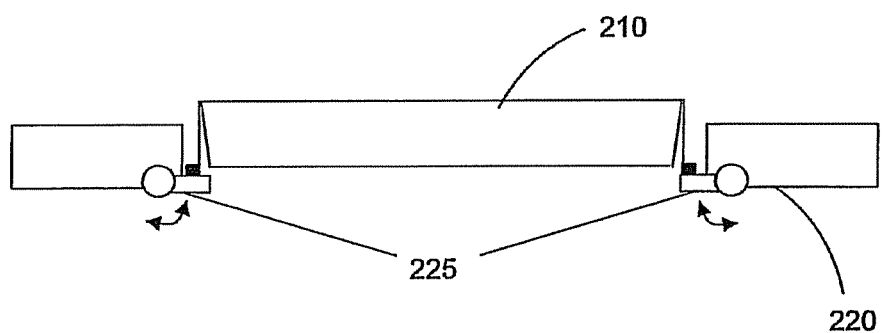
FIG. 2 provides a schematic showing a microplate plate lowering mechanism with the nested microplate in an up or rest position.
Figure 3:
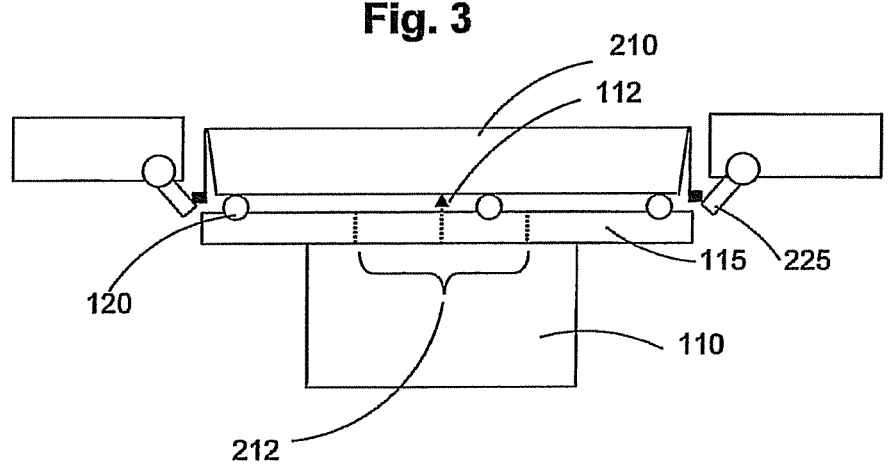
FIG. 3 shows the lowering mechanism in a down or engaged position lowering the nested microplate of FIG. 2 onto a reference plane with mounting features.

In embodiments, the system can include a positioning system mechanism or component as shown in FIGS. 2 and 3, such as rests 225 attached to frame or skirt mount nest member 220, or like mechanism or component, which mechanism or component can change the relative separation between the microplate 210 and the optical reader 110. For example, simple opposite rotation of the rests relative to the 225 members lowers the microplate 210 onto, for example, the mount features 120. A significant aspect is that when the microplate 210 is lowered onto the mount features 120, the plate 210 is no longer necessarily constrained by the nest member 220 in the vertical or z direction. While the nest can still constrain the microplate in the lateral direction, it may not be necessary to so constrain the microplate, depending on the sensitivity of the optical system, i.e., the reader and the microplate sensors, to lateral displacement.

Figure 4:
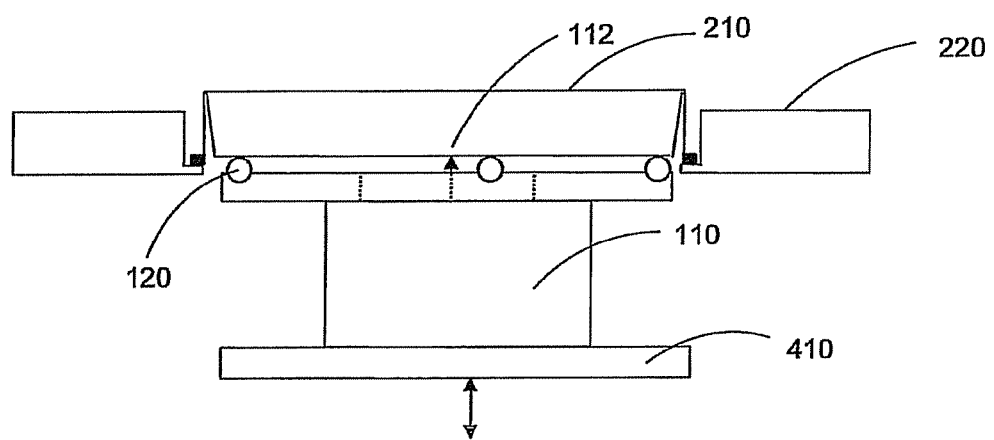
FIG. 4 is a schematic showing a microplate in a first nested position.
Figure 5:
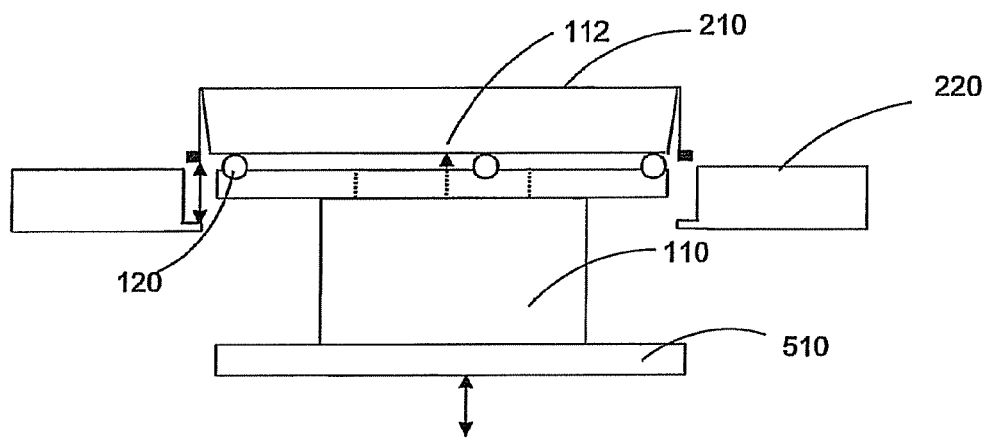
FIG. 5 shows the nested microplate of FIG. 4 lifted out of the nest by a lift or elevator mechanism and engaged with the mounting features of reference plane atop the optical reader.

An alternative to reversibly lowering the microplate onto the optical reader via the lowering rest mechanism in the nest as shown in FIG. 3 is to reversibly raise the optical reader to lift the microplate out of the nest as shown in FIGS. 4 and 5. The lifting mechanism can be, for example, an elevator 510 which is depicted as a functional box in the drawings.

Figure 6A:
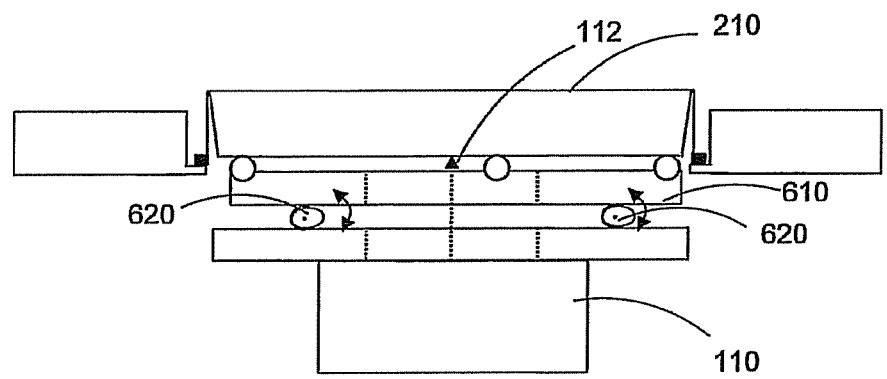
FIGS. 6A and 6B are schematics showing a lift mechanism between the reference plane and the optical reader adapted to reversibly nest 6A and to lift 6B the microplate to contact the mounting features of the reference plane.
Figure 6B:
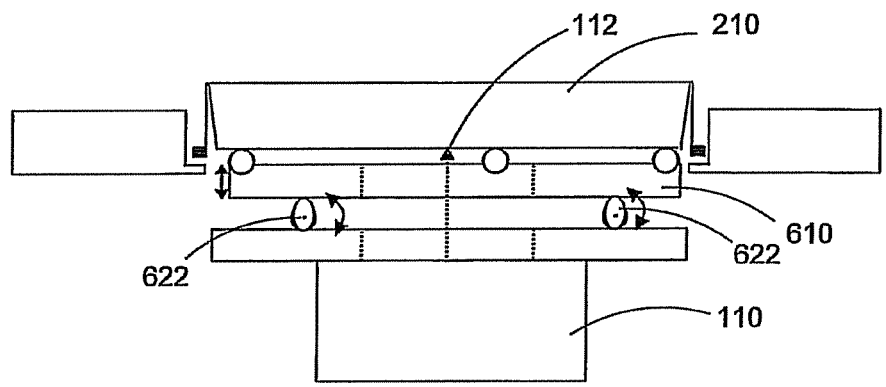

Alternatively, the lifting mechanism can be, for example, a cam drive, such as cam 620 (shown in a lowered position) and 622 (raised position) of FIG. 6 such that only the reference plane is raised to, in turn, lift the microplate, while the reader remains stationary. The lifting mechanism can alternatively be integrated into the reference plane.

Variations or alternative implementations of the microplate lowering and microplate lifting mechanisms are shown in FIGS. 3, 5, 6, and 10. A significant aspect of either or both operations is that they can essentially remove the label-free microplate from the constraint of the nest and decouple the label-free measurement from mechanical perturbations resulting from the surrounding mechanical and motion subsystems.

Figure 7:
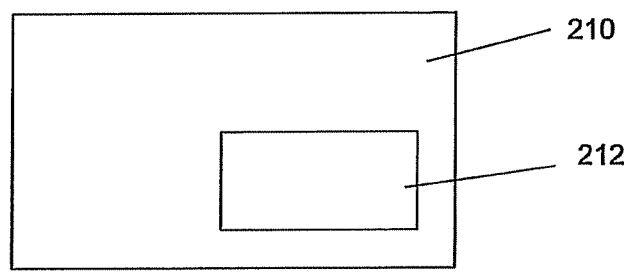
FIG. 7 is an illustration of the optical reader having an aperture that interrogates a limited portion of a microplate.

The disclosed system can eliminate the need for precision mechanical stages when, for example, shuttling a label-free microplate 210 over an optical reader 110 to required locations for interrogation. To accommodate this shuttling, one only needs to add additional mount features 120 to the reference plane in order to control the angle of incidence through the Z displacement at the various microplate locations. Consider, for example, the situation where a particular reader 110 and reader aperture 212 can only read a quarter of a microplate 210 at one time, that is, about one fourth of the microplate's biosensor area per unit time, such as shown in FIG. 7.

To measure an entire microplate 210, the microplate can be moved by, for example, mechanical stages, to place successive quarters of the microplate area in alignment with the reader aperture 212. If only stages are used to accomplish this motion without the disclosed system, then the stages and surrounding mechanical components must maintain the interrogating optical signal incidence angle on the microplate to within the tolerance necessary to achieve acceptable performance of the label-free measurement. However, if the disclosed system is used then the angular position of the microplate relative to the optical reader is decoupled from the stages and surrounding mechanical components and the incidence angle is controlled through the mount features. Hence, inexpensive stages can be used to manipulate the plate over the reader while a high degree of control is maintained over the interrogating optical signal incidence angle. To achieve this, additional mount features such as those shown in FIG. 8 may be needed on the mechanical reference plane.

Figure 8:
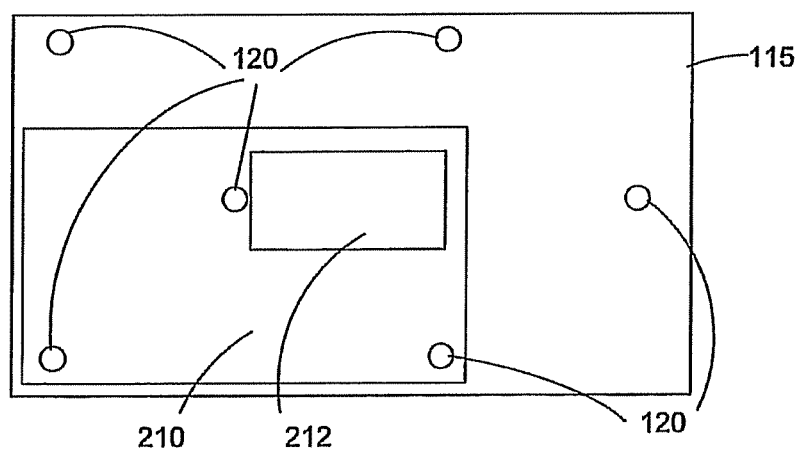
FIG. 8 is an illustration of a mount system configured to accommodate a quarter plate reader and plate motion using six mounting features.

FIG. 8 shows a configuration to accommodate a quarter-plate optical reader. The mechanical reference surface or plane 115 uses six mounting features 120. Other configurations can be envisioned that use greater or fewer mounting features and that could accommodate optical readers that can access different sized regions of a microplate 210. The four plate positions accommodated by the six mount feature configuration illustrated in FIG. 8 are shown in FIGS. 9A to 9D. Here only three mount features are used for any given microplate position. In each of the four microplate positions in FIG. 9 the microplate is either lowered or lifted onto the corresponding mount features to set the interrogating optical signal incidence angle via the aforementioned mechanisms. The disclosure includes the incorporation of raised mount features on the mechanical reference plane. In embodiments, the disclosure also includes incorporating recessed mount features 1015 on the reference plane. In embodiments, a double-sided kinematic insert 1010 can be positioned, such as in the configuration as shown in FIG. 10.

Figure 10:
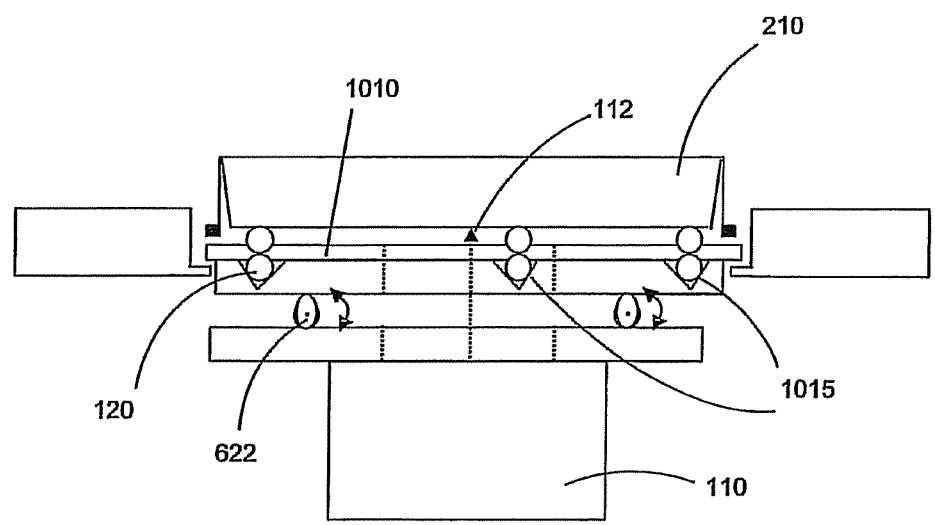
FIG. 10 shows an example of kinematic mounting features recessed in the reader reference plane and having a double-sided kinematic insert configuration.

In embodiments, including the combination of recessed mount features and the double sided kinematic insert of FIG. 10, the microplate 210 can be either lowered or raised (e.g., lifted or pushed upward) into the corresponding recessed kinematic features on the reference plane to set the interrogating optical signal incidence angle via the aforementioned mechanisms.

Figure 11:
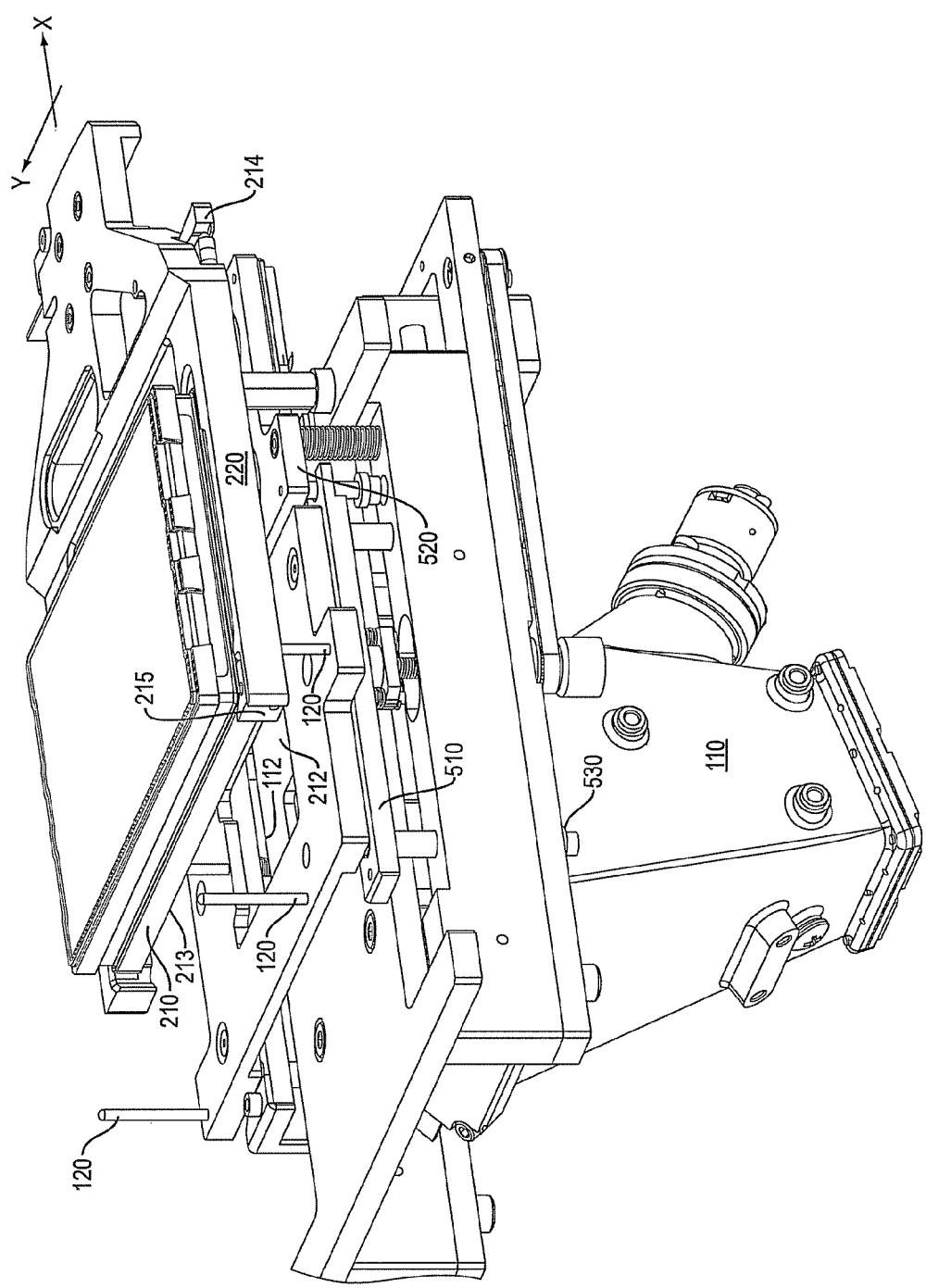
FIG. 11 shows a perspective of an exemplary mount system having a vertically movable or adjustable plane having mounting features extending from the reader reference plane to elevate the nested microplate, and a shuttle for relative alignment motion of the microplate.

FIG. 11 shows a perspective of an exemplary mount system having a vertically movable or adjustable reference plane 115 with strategically placed mounting features 120. In the system shown, the mounting features are shaped pins extending upwardly from the reference plane. An elevator 510 raises the reference plane 115 to engage the mounting features with the bottom 213 of a microplate 210, to control the z-displacement of the microplate from an optical reader that interrogates the microplate through an aperture 212 in the reference plane. The z-displacement, in turn, controls the angle of incidence of the optical reader beam 112 at the microplate 210.

A carrier 220 grips and releases the microplate 210 in cooperation with the movement of the reference plane 115 by the elevator 510. The carrier 210 includes a spring clamp 215 used for gripping and releasing the microplate. A plate release mechanism 520 includes release cams (not shown) that rotate in one direction to operate a clamp release arm 214 to open or release the clamp 215 and thus release the microplate 210 from the carrier 220. The release cams rotate in an opposite direction to direct the arm 214 to apply the clamp 215 and thus grip the microplate 210 into the carrier 220. The clamp 215 may but need not be preloaded for movement in one or both directions.

A shuttle (not shown) operates in a known manner to move the carrier 220, and thus, the microplate 210, relative to the reference plane 115 in the x and y directions as indicated by the x and y arrows in the drawing. When the shuttle has moved the carrier 220 and microplate 210 to a desired position for interrogation, the system operates the plate release mechanism 520 in cooperation with the elevator 510, such that the carrier releases and grips the microplate as the elevator raises and lowers the reference plane 115 to engage the mount features 120 with and disengage the mount features 120, here pins, from the bottom 213 of the microplate 210. As the elevator 510 raises the reference plane 115 and brings the pins into contact with the bottom 213 of the microplate 210, the system rotates the release cams to control the spring clamp 215 and release the microplate 210 from the carrier 220. The z-displacement of the microplate 210 is then controlled through further movement of the reference plane 115, and thus, through contact with the pins. The reference plane 115 is moved to position the microplate 210 at a desired height relative to the reader. In particular, the system positions the bottom 213 of the microplate 210 at or near the focal point of the reader optics and thus controls the angle of incidence of the interrogation beam at the microplate 210.

The system may next rotate the release cams to operate the clamp 215, such that the microplate 210 is again gripped by the carrier 220. Depending on the tolerance of the system, once the microplate 210 is engaged by the mounting features 120 the re-gripping of the microplate 210 by the carrier 220 may not be necessary.

To repeatedly control the z-displacement of the bottom 213 microplate 210 from the reader optics, and thus, the angle of incidence of the interrogation beam at the microplate 210, one or more mechanical stops 530 may be included in the elevator mechanism, such that the reference plane is raised until the one or more stops are met. The stops may be mechanical stops as shown, or alternatively, the stops may be associated with the movement of, for example, a stepper motor, and consist of a step count from a predetermined starting position. Using the stops, the system repeatedly positions the bottom 213 of the microplate 210 at a predetermined height relative to the optical reader 110, to predictably and repeatedly control the angle of incidence of the optical reader interrogation beam 112 at the microplate 210.

In addition, to ensure that the reference plane 115 is parallel to the orientation of the optical reader mechanism, and thus, that the pins are normal to the reader mechanism when the reference plane 115 is in a final position for an interrogation of the microplate 210, deformable washers (not shown) may be included between the reference plane 115 and components of the elevator 510 that contact the reference plane.

If the optical reader 110 is capable of interrogating the entire microplate 210 from a single scan position, the mounting features 120 are strategically located on the reference plane 115 to correspond to a perimeter of the microplate surrounding the array of wells. The mounting features 120 thus do not interfere with the interrogation of the wells by the optical reader 110. A minimum of three mounting features 120 positions the microplate 210 such that a plane represented by the bottom 213 of the microplate 210 is held parallel to the reading mechanism of the optical reader 110, and at a predetermined height relative to the optical reading mechanism to control the angle of incidence of the interrogation beam 112 at the microplate 210. As discussed, the microplate 210 is positioned by the mounting features 120 in the z direction at or near the focal length of the reader optics.

If the optical reader 110 is capable of interrogating only a portion of the microplate 210, more than three mounting features are required, in order to engage the microplate 210 in the various positions to which the microplate must be moved relative to the aperture 212 for a complete interrogation. As discussed above with reference to FIG. 9, the mounting features 120 are arranged such that at least three mounting features are in contact with the bottom 213 of the microplate 210 when the microplate 210 is in the various positions for interrogation by the reader 110.

To position the microplate 210 relative to the aperture 212 at the respective locations to interrogation, the shuttle moves the carrier 220 relative to the reference plane 115, in the example the movement is in the x and y directions. The shuttle operates in cooperation with the elevator 510, such that the shuttle moves the carrier 220, which is then gripping the microplate 210, when the reference plane 115 is in a lowered position and the mounting features 120 are disengaged from the bottom 213 of the microplate 210. Since the angle of incidence of the optical reader interrogation beam 112 at the microplate 210 is controlled by the mounting features 120, the shuttle may be relatively inexpensive, and thus imprecise, without adversely affecting the repeatability of the interrogation of the microplate 210 by the reader 110. For example, the shuttle may have a 200 micrometer accuracy, about 3 milliRad of wobble, and about 30 micrometers of resolution.

At each location, the system operates as described above to control the angle of incidence when the interrogation is complete at one location, the system repeats the process by moving the microplate to a next location and so forth.

The pins utilized as mounting features 120 in the system of FIG. 11 are rounded and polished on the end that engages the bottom 213 of the microplate 210, such that the pins engage the bottom of the microplate as essentially points, without requiring pointed ends. Notably, kinematic adjustment features are not required.

The interrogation process can be readily and reliably repeated after the microplate 210 is removed from the carrier 220 and replaced, since the desired angle of incidence of the interrogation beam at the microplate can be reliably and repeatedly reproduced at any and all microplate interrogation positions using the mounting system described above. Accordingly, the mounting system is particularly well suited for use with protocols that require the before and after interrogations discussed above.

What is claimed is:

1. A microplate mounting system to mount a microplate relative to an optical reader to control an angle of incidence of an interrogation beam at the microplate comprising:
   a nest for receiving a well plate;
   a microplate with a bottom and a skirt;
   a reference plane with at least one set of mount features; and
   a positioning mechanism that provides a reversible and predetermined separation in the z direction between a plane formed by the bottom of the microplate and the optical reader to control the angle of incidence of the interrogation beam at the microplate by reversibly controlling the relative positioning of the microplate in the z direction through an engagement between one or both of the bottom of the microplate and the skirt of the microplate and one of the at least one set of mount features so that the microplate is no longer constrained by the nest in a vertical direction.

2. The system of claim 1 wherein the one set of mount features includes at least three features.

3. The system of claim 2 wherein the positioning mechanism lowers the microplate until one or both of the bottom of the microplate and the skirt of the microplate engages the one set of mount features.

4. The system of claim 2 wherein the positioning mechanism elevates the reference plane to engage the one set of mount features and one or both of the bottom of the microplate and the skirt of the microplate.

5. The system of claim 4 wherein the position mechanism further elevates the reference plane to elevate the microplate.

6. The system of claim 2 wherein the nest is configured to:
   grip the microplate to position the microplate relative to the reference plane, and
   release the microplate when the bottom of the microplate and the one set of mount features engage.

7. The system of claim 6 wherein the nest re-grips the microplate when the microplate is at a predetermined separation from the optical reader in the z direction.

8. The system of claim 7 wherein the first positioning mechanism is integral to the reference plane, the nest, the optical reader, or a combination thereof.

9. The system of claim 2 wherein the one set of mount features comprise from 4 to 10 spheres, pins, vias, or a combination thereof, attached to the reference plane.

10. The system of claim 9 wherein the one set of mount features are partially embedded in the reference plane.

11. The system of claim 1 wherein the first positioning mechanism comprises a cam, a cantilever, a spring, a manual or automated elevator, a linear actuator, a stepper motor, or a combination thereof.

12. The system of claim 1 further comprising a second positioning mechanism that provides relative lateral alignment motion between the microplate and the reference plane.

13. The system of claim 12 wherein the second positioning mechanism provides the relative lateral alignment motion as vibrational, circular, elliptical, rectangular or simple rectilinear motion, or a combination thereof.

14. The system of claim 13 wherein the second positioning mechanism moves the microplate about at least a portion of an aperture in the reference plane.

15. The system of claim 1 wherein the one set of mount features comprises an insert member having at least three mount features on each side of the insert, the insert being situated between the reference plane and the microplate.

16. The system of claim 15 further comprising at least one of:
   the reference plane having a recess adapted to receive at least one mount features on the insert,
   the microplate having a recess adapted to receive at least one mount features on the insert, or
   a combination thereof.

17. The system of claim 15 further comprising a second positioning mechanism providing relative lateral alignment motion between the microplate and the reference plane.

18. The system of claim 17 wherein the second positioning mechanism moves the microplate about at least a portion of an aperture in the reference plane.

19. A method of using the microplate mounting system of claim 1 comprising:
   positioning the microplate relative to the reference plane; and
   engaging one or both of the bottom of the microplate and the skirt of the microplate and the one set of mount features to control the angle of incidence by controlling the separation in the z direction between the bottom of the microplate and the optical reader.

20. The method of claim 19 wherein the engaging is accomplished by reducing the relative separation between the reference plane and the microplate in the z direction.

21. The method of claim 19 further comprising
   providing relative lateral alignment motion between the microplate and the reference plane when the one or both of the bottom of the microplate and the skirt of the microplate and the one set of mount features are not engaged, and
   when lateral movement is completed, engaging one or both of the microplate bottom and skirt and the one set of mount features to control the angle of incidence.

22. The method of claim 19 wherein the relative lateral alignment motion moves the microplate in a plane parallel to the reference plane and in a concentric or in a rectangular eccentric pattern about an aperture in the reference plane.

23. The method of claim 22 wherein the relative lateral alignment motion moves the microplate about at least a portion of an aperture in the reference plane.

24. The method of claim 19 wherein
   the microplate is positioned through insertion in and movement with the nest,
   the microplate is removed from the nest and reinserted into the nest, and the microplate is re-positioned in the z direction relative to the optical reader by a re-engaging of one or both of the bottom and the skirt of the reinserted microplate and the one set of mount features such that the relative level of the bottom of the reinserted microplate varies from the original level of the bottom of the microplate by from about 1 microRadians to about 500 microRadians.

25. The method of claim 19 wherein the one or both of the microplate and the reference plane are moved to engage one or both of the bottom and skirt of the microplate and the one set of mount features.

* * * * *

UNITED STATES PATENT AND TRADEMARK OFFICE
CERTIFICATE OF CORRECTION

PATENT NO. : 8,614,789 B2
APPLICATION NO. : 13/032303
DATED : December 24, 2013
INVENTOR(S) : David Noblett et al.

It is certified that error appears in the above-identified patent and that said Letters Patent is hereby corrected as shown below:

In the Claims:
Claim 16, col. 12, line 25:
~~least one mount features on the insert,~~
least one mount feature on the insert Claim 16, col. 12, line 27:
~~one mount features on the insert, or~~
one mount feature on the insert, or Signed and Sealed this
Twenty-fifth Day of February, 2014

Michelle K. Lee
*Deputy Director of the United States Patent and Trademark Office*